(12) United States Patent
Singhal et al.

(10) Patent No.: US 9,670,308 B2
(45) Date of Patent: Jun. 6, 2017

(54) DEVICE AND METHOD FOR TREATMENT OF OPENINGS IN VASCULAR AND SEPTAL WALLS

(71) Applicants: Lawrence Livermore National Security, LLC, Livermore, CA (US); The Texas A&M University System, College Station, TX (US)

(72) Inventors: Pooja Singhal, Dublin, CA (US); Thomas S. Wilson, San Leandro, CA (US); Elizabeth Cosgriff-Hernandez, College Station, TX (US); Duncan J. Maitland, College Station, TX (US)

(73) Assignees: Lawrence Livermore National Security, LLC, Livermore, CA (US); The Texas A&M University System, College Station, TX (US)

(*) Notice: Subject to any disclaimer, the term of this patent is extended or adjusted under 35 U.S.C. 154(b) by 488 days.

(21) Appl. No.: 13/797,727

(22) Filed: Mar. 12, 2013

(65) Prior Publication Data

US 2013/0317541 A1 Nov. 28, 2013

Related U.S. Application Data

(60) Provisional application No. 61/651,477, filed on May 24, 2012.

(51) Int. Cl.
*A61B 17/08* (2006.01)
*C08G 18/66* (2006.01)
(Continued)

(52) U.S. Cl.
CPC ...... *C08G 18/6622* (2013.01); *A61B 17/0057* (2013.01); *C08G 18/10* (2013.01); *C08G 18/14* (2013.01); *C08G 18/165* (2013.01); *C08G 18/73* (2013.01); *C08G 63/00* (2013.01); *C08G 63/6852* (2013.01); *C08G 71/04* (2013.01); *C08J 9/00* (2013.01);
(Continued)

(58) Field of Classification Search
CPC ...... A61B 17/0057; A61B 2017/00623; A61B 2017/00606; A61B 2017/00592; A61F 2/064; A61F 2210/0014; A61F 2210/0033
USPC ............... 606/213, 214, 200, 151, 153–156; 128/887
See application file for complete search history.

(56) References Cited

U.S. PATENT DOCUMENTS

| 3,989,676 A | 11/1976 | Gerkin et al. |
| 5,049,591 A | 9/1991 | Hayashi et al. |

(Continued)

OTHER PUBLICATIONS

Eick, "Temperature Controlled Radiofrequency Ablation," Indian Pacing and Electrophysiology Journal, www.ipej.org, 1994, pp. 66-73.

(Continued)

*Primary Examiner* — Melanie Tyson
*Assistant Examiner* — Erich Herbermann
(74) *Attorney, Agent, or Firm* — Eddie E. Scott

(57) ABSTRACT

A device, system and method for treatment of an opening in vascular and/or septal walls including patent foramen ovale. The device has wings/stops on either end, an axis core covered in a shape memory foam and is deliverable via a catheter to the affected opening, finally expanding into a vascular or septal opening where it is held in place by the expandable shape memory stops or wings.

22 Claims, 5 Drawing Sheets

(51) Int. Cl.
| | |
|---|---|
| A61B 17/00 | (2006.01) |
| C08G 63/00 | (2006.01) |
| C08G 63/685 | (2006.01) |
| C08G 71/04 | (2006.01) |
| C08J 9/00 | (2006.01) |
| C08G 18/10 | (2006.01) |
| C08G 18/08 | (2006.01) |
| C08G 18/16 | (2006.01) |
| C08G 18/73 | (2006.01) |
| C08G 101/00 | (2006.01) |

(52) U.S. Cl.
CPC ........... *A61B 2017/00592* (2013.01); *A61B 2017/00606* (2013.01); *A61B 2017/00623* (2013.01); *C08G 2101/005* (2013.01); *C08G 2101/0083* (2013.01); *C08G 2230/00* (2013.01); *C08G 2280/00* (2013.01); *C08J 2375/06* (2013.01)

(56) References Cited

U.S. PATENT DOCUMENTS

| | | | |
|---|---|---|---|
| 5,192,301 | A * | 3/1993 | Kamiya et al. ............... 606/213 |
| 5,571,857 | A | 11/1996 | Gruber et al. |
| 5,634,936 | A * | 6/1997 | Linden et al. ............... 606/213 |
| 5,770,635 | A | 6/1998 | Lee et al. |
| 5,853,422 | A * | 12/1998 | Huebsch et al. ............. 606/213 |
| 5,986,039 | A | 11/1999 | O'Brien et al. |
| 7,300,961 | B2 | 11/2007 | Haider et al. |
| 7,338,983 | B2 | 3/2008 | Simpson et al. |
| 8,133,256 | B2 | 3/2012 | Wilson et al. |
| 8,882,697 | B2 * | 11/2014 | Celermajer et al. ............ 604/8 |
| 2003/0236314 | A1 | 12/2003 | Haider et al. |
| 2004/0176799 | A1 * | 9/2004 | Chanduszko et al. ........ 606/213 |
| 2005/0182428 | A1 * | 8/2005 | Bearinger et al. ............ 606/151 |
| 2006/0036045 | A1 | 2/2006 | Wilson et al. |
| 2007/0293891 | A1 * | 12/2007 | Corcoran et al. ............. 606/213 |
| 2009/0253816 | A1 | 10/2009 | Nascimento et al. |
| 2009/0313909 | A1 | 12/2009 | Clatty et al. |
| 2010/0131006 | A1 * | 5/2010 | Chanduszko ................. 606/213 |
| 2010/0145382 | A1 * | 6/2010 | Chanduszko ................. 606/213 |
| 2010/0152312 | A1 | 6/2010 | Burdeniuc et al. |
| 2010/0234880 | A1 * | 9/2010 | Abbott et al. ................ 606/213 |

OTHER PUBLICATIONS

Ashby et al. "The Mechanical Properties of Cellular Solids," The Metallurgical Society of AIME, Materials, Metallurgical Transactions A, vol. 14A, pp. 1755-1769, (1983).
Busby et al., "Emulsion-Derived Foams (PolyHIPEs) Containing Poly(E-caprolactone) as Matrixes for Tissue Engineering," Biomacromolecules, vol. 2, No. 1, pp. 154-164, (2001).
Christenson et al., "Biodegradable Fumarate-Based PolyHIPEs as Tissue Engineering Scaffolds," Biomacromolecules, vol. 8, No. 12, pp. 3806-3814, (2007).
El Feninat et al., "Shape Memory Materials for Biomedical Applications," Adv. Eng. Materials, 4, No. 3, pp. 91-104, (2002).
Gibson et al., "The Mechanics of Two-Dimensional Cellular Materials," Proc. R. Soc. Lond. A, vol. 382, No. 1782, pp. 25-42, (1982).
Kim et al., "Dynamic Film and Interfacial Tensions in Emulsion and Foam Systems," J. of Colloid and Interface Sci. 187, pp. 29-44, (1997).
Lendlein et al., "Biodegradable, Elastic Shape-Memory Polymers for Potential Biomedical Applications," Science, vol. 296, pp. 1673-1676 (2002).
Lendlein et al., "Degradable, Multifunctional Polymeric Biomaterials with Shape Memory," In: Van der Biest, M. Gasik, & J. Vleugels) (Eds._: Functionally Graded Materials VIII, Materials Science Forum, FGM2004, 8th Int'l Symposium. vol. 492-493 Leuven (b), and Engineering, eds O. V(Trans Tech Publ, Switzerland).
Lendlein et al., "AB-polymer networks based on oligo (E-caprolactone) segments showing shape-memory properties," PNAS, vol. 98, No. 3, pp. 842-847, (2001).
Maitland et al., "Prototype laser-activated shape memory polymer foam device for embolic treatment of aneurysms," J. of Bio. Optics, vol. 12 (3), 030504-1 0 030504-3, (2007).
Meier, et al., "Synthesis and Characterization of 4—and 6-arm Star-Shaped Poly(E-Caprolactone)s", e-Polymers, 2005, No. 085. pp. 1-8.
Min et al., "Biodegradable shape-memory polymer-polylactide-co-poly(glycolide-co-caprolactone) multiblock copolymer," Polym. Adv. Technol., 16, pp. 608-615 (2005).
Nagata et al., "Photocurable biodegradable poly(E-caprolactone)/poly (ethylene glycol) multiblock copolymers showing shape-memory properties," Colloid Polym Sci. 284, pp. 380-386 (2006).
Rickert et al., "In vitro Cytotoxicity Testing of AB-polymer Networks Based on Oligo(E-caprolactone) Segments after Different Sterilization Techniques," J. of Bio. Materials Research Part B: Applied Biomaterials 67, pp. 722-731 (2003).
Rickert et al., "Cell proliferation and cellular activity of primary cell cultures of the oral cavity after cell seeding on the surface of a degradable, thermoplastic block copolymer," Biomedizinische Technik, Biomedical Eng. 50, 92 (2005).
Shah et al., "A correlation of foam stability with surface shear viscosity and area per molecule in mixed surfactant systems," Colloid & Polymer Sci. 256, pp. 1002-1008, (1978).
Small, et al., "Shape Memory Polymer Stent with Expandable Foam: A New Concept for Endovascular Embolization of Fusiform Aneurysms," IEEE Transactions on Biomedical Engineering, vol. 54, No. 6, pp. 1157-1160, (2007).
Sokolowski et al., "Medical applications of shape memory polymers," Institute of Physics Publishing, Biomed. Mater. 2, pp. S23-S27, (2007).
Tabor et al., "The effect of polyol functionality on water blown rigid foams,". J. of Cellular Plastics 33, 372 (1997).
Thirumal et al., "Effect of Foam Density on the Properties of Water Blown Rigid Polyurethane Foam," J. of App. Poly. Sci., vol. 108, pp. 1810-1817, (2008).
Tobushi et al., "The influence of shape-holding conditions on shape recovery of polyurethane-shape memory polymer foams," Institute of Physics Publishing, Smart Mater. Struct. 13, pp. 881-887, (2004).
Wilson et al., "Shape Memory Polymers Based on Uniform Aliphatic Urethane Networks," J. of App. Polym. Sci., vol. 106, pp. 540-551, (2007).
International Search Report and Written Opinion for PCT/US13/041894 corresponding to U.S. Appl. No. 13/797,631, 9 pp.

* cited by examiner

DEVICE AND METHOD FOR TREATMENT OF OPENINGS IN VASCULAR AND SEPTAL WALLS

CROSS-REFERENCE TO RELATED APPLICATIONS

This application claims benefit under 35 U.S.C. §119(e) of U.S. Provisional Patent Application No. 61/651,477 filed May 24, 2012 entitled "Ultra-Low Density Biodegradable Shape Memory Polymer Foams with Tunable Physical Properties," the disclosure of which is hereby incorporated by reference in its entirety for all purposes.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

Field of Endeavor

A device, system and method for treatment of an opening in vascular and/or septal walls including patent foramen ovale.

State of Technology

Patent Foramen Ovale

Patent Foramen Ovale ("PFO") is a genetic condition in which a remnant fetal opening in the septal wall causes shunting of unfiltered blood to the systemic circulation. This opening serves an important physiologic function during fetal development when blood is oxygenated by the mother, and after birth it typically closes due to the increased pressures in the heart. However, it is reported that in nearly 27% of the population it remains as an opening with a flap-like structure, and therefore, has the potential for allowing blood to pass directly from the right side of the heart to the left side of the heart. When this occurs, the blood bypasses the pulmonary system and clots present in the blood are not filtered out. These clots then pass directly to the systemic system, where they can lead to stroke. Of the cases of cryptogenic stroke, constituting 40% of all stroke cases, the occurrence rate of PFO is about 50-54%, as compared to 10-15% in control patients. Thus, PFO has been found to be involved in 20-22% of all stroke incidences. Incidences of stroke in such cases have been found to have a direct correlation with size of the septal opening and the degree of shunting caused, based on patient's physical activity. PFO has also been shown to be associated with other severe conditions like myocardial infarction, peripheral embolism, decompression illness, migraines and hypoxaemia to name a few.

Current Treatment of PFO

Present treatments for PFO include medical therapy, such as anticoagulants, surgical repair, and transcatheter insertion of a device for sealing the opening. For the closure, percutaneous procedure is preferred over surgical repair and devices available on the market for this procedure include Amplatzer, PFO-Star, Clamshell Septal Umbrella, CardioSEAL septal occluder, and buttoned devices, among others. These devices sandwich the septal wall or occlude the opening in order to prevent leakage between the atria and to create a seal. Significant difference in performance among these devices has been reported with Amplatzer, designed with Nitinol based shape memory alloy frame that is filled with biodegradable polyester material, being the most commonly used. Residual shunting is common even after the transcathetral procedure and is found in about 50% subjects immediately after closure, and in about 40% subjects one month after closure.

Other Septal Defects

PFOs are a variation of atrial septal defects (ASDs) known as ostium secundum, which describes septal defects located near the center of the septum. Other common forms of ASD are ostium primum, which occur near in the lower part of the septum and are accompanied by an associated cleft in the mitral valve resulting in mitral regurgitation, and sinus venosus that are often accompanied by an anomalous pulmonary venous connection. Ostium primum and sinus venosus typically require surgical repair. Ventricular septal defects (VSD) are actually the most common form of congenital heart defect, and may be treated with transcatheter delivered septal occlusion devices. As with ASD, many different classifications of VSD describe the form, location, and hemodynamic implications. While VSD closure via transcatheter therapy is considered more challenging due to variations in position, form and location, two types of VSD have emerged as favorable candidates for transcatheter closure: muscular and perimembranous VSDs. Also, more recently, VSDs resulting from septal rupture induced by myocardial infarction have been targeted for transcatheter device closure. Presently, devices very similar to those used to treat PFO and ASD are employed to treat VSD in qualified candidates, i.e. the concept is the same, and however the geometry of the device varies. Ostium secundum ASDs, and muscular and perimembranous VSDs can potentially be treated by the device of this invention.

Shape Memory Polymers (SMPs)

Thermally actuated shape memory polymers (SMPs) have the ability to transform from a stable "secondary" shape to a predetermined "primary" shape when heated or otherwise activated. This ability stems from the polymer morphology, which is generally described as consisting of a shape-fixing matrix phase (amorphous or semi-crystalline polymer) and a shape memorizing dispersed phase (physical or chemical crosslinks). The "primary" shape is typically programmed into the material during its original melt processing or curing process. The temporary "secondary" shape is obtained by deforming the material while heating it above the characteristic thermal transition temperature, Tt, and then cooling to fix the shape. Tt can be either the glass transition Tg, or melting, Tm, temperature depending on the polymer system. A detailed description of the fundamental principles of shape memory behavior is given by Lendlein and Kelch (Lendlein, A. and S. Kelch, *Shape-memory polymers.* Angew Chem Int Ed, 2002. 41: p. 2034-2057).

A number of SMP-based medical devices have been proposed. A recent review of thermally actuated SMPs in medicine can be found in Small, W., P. Singhal, T. S. Wilson, and D. J. Maitland, *Biomedical applications of thermally activated shape memory polymers.* Journal of Materials Chemistry, 2010. 20 (17): p. 3356-3366. SMP biomedical applications include thrombectomy devices to treat ischemic stroke, embolic coils to fill aneurysms, and vascular stents. Encouraging biocompatibility data (Cabanlit, M., D. J. Maitland, T. S. Wilson, S. Simon, T. Wun, M. E. Gershwin, and J. Van de Water, *Polyurethane shape-memory polymers demonstrate functional biocompatibility in vitro* Macromol Biosci 2007. 7: p. 48-55) and the recent, first SMP, approval by the FDA of a shoulder anchor device (Melkerson, M. N. *Food and Drug Administration* 510(*k*) *approval of Medshape Solution's SMP shoulder anchor.* 2009; Available from the website of the Food and Drug Administration (www.fda.gov/cdrh/pdf8/K083792.pdf) have been reported for SMP materials.

Biodegradable SMPs

The importance of biodegradability of polymeric materials has long been acknowledged, and several comprehensive reviews have been published on them as early as 1990s (See Albertsson, A. and S. Karlsson, *Chemistry and Biochemistry of Polymer degradation*, in *Chemistry and technology of biodegradable polymers*, G. J. L. Griffin, Editor. 1994, Blackie Academic & Professional, an imprint of Chapman & Hall: Glasgow, UK. p. 48 and Amass, W., A. Amass, and B. Tighe, *A review of biodegradable polymers: uses, current developments in the synthesis and characterization of biodegradable polyesters, blends of biodegradable polymers and recent advances in biodegradation studies.* Polymer International, 1998. 47 (2): p. 89-144). Timeframes for the biodegradation of the most popular polymers have been compared by Holland et. al. (Holland, S. J., *Novel polymeric controlled release systems.* 1986, Aston University: Birmingham). Also the effect of the media pH has been studied and it has been shown that increase in hydrophilicity increases the rate of degradation of materials. Biodegradable materials have been shown to have very different degradation timeframes in-vitro and in-vivo due to the enzymatic factors and in vivo physiological conditions (abiotic vs. biotic degradation). When the mechanism of degradation is primarily hydrolytic cleavage of bonds, in-vitro and in-vivo results are shown to have better agreement.

Some known biodegradable polymers include polycaprolactonediols (PCL) that were either reacted with acrylic monomers and photocured to get a SMP network, or reacted with a diisocyanate to make a polyurethane. Biodegradability and shape memory behavior of 4,4-(adipoyldioxy)dicinnamic acid and poly(ethylene glycol) has also been studied. PCL based polymers typically show lower degradation rate, lower shape recovery and low mechanical strengths. In another series of investigations PLA based polyurethanes were developed and mechanical and shape memory properties were investigated for them. These showed better shape recovery but much higher actuation temperatures. Subsequently multiple copolymers based on PLA and PCL were reported to adjust shape memory behavior, biodegradability and actuation temperature to a desirable range. Other known biodegradable SMPs include amorphous copolyester urethane networks, poly(3-hydroxybutyrate)-co-(3-hydroxy valerate).

SMP Foams

The unique actuating properties of SMPs can be enhanced further through their structuring into low-density open cell foams. For example, a model isotropic SMP open cell foam should have an initial modulus that scales as the square of the solid volume fraction ($\phi s$) and a yield stress which scales with volume fraction to the 3/2 power. SMP foam with a solid volume fraction of 0.01 would be expected to have a modulus 0.0001 times that of neat SMP, with proportional decreases in recovery stress during actuation. Likewise, structuring SMP into foams significantly increases the range of strains (particularly volume changes) accessible to SMP devices, which can now be compressed into a very compact temporary form and thermally actuated to expand back to its original form.

It has been demonstrated that SMP foams with densities as low as 0.005 g/cc, corresponding to volume expansions in excess of a 100 times from a fully compressed shape can be made. While foams made using the process of pore templating via salt leaching are now common to tissue engineering applications, the resulting foams have relatively poor mechanical properties as compared to foams made by blowing methods. At the same time chemical and physical blowing processes are rare for materials with highly cross-linked molecular structures.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The invention is a device, a system and method for treatment of vascular and septal openings. The device comprises a structure made from biocompatible components, wherein the combined components comprise a structure having two opposing stops or wings, a distal wing and a proximal wing, connected by an axis that is covered by a shape memory polymer foam, wherein the wings when expanded are planar with the surface in which the opening is to be disposed, the wings being larger in surface area than the diameter of the opening and can be collapsed into a secondary shape that together with the other components of the device may be disposed inside a vascular catheter.

The system of the invention comprises a device as described above; a catheter to carry the device when it is in its secondary shape to the location of deployment; a carrier wire on which the device when it is in its secondary shape is carried inside the catheter; a pusher to move the device into the desired location; and a releasable connector that connects the device to the pusher.

The method consists of inserting a vascular catheter into a blood vessel of a patient having a vascular or septal opening to be treated and moving it to the proximate site of the opening to be treated, the catheter having disposed in it a device as described above having a proximal wing and a distal wing to be delivered to the opening to be treated. The device is carried over a guide wire being moved by a pusher and the distal wing of the device deployed into the opening by pushing the device out of the catheter into the opening and the distal wing through the opening and the connector axis deployed in the opening with the other wing on the opposite side of the wall of the opening and wherein the shape memory polymer of the device is activate to assume its primary shape.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF SPECIFIC EMBODIMENTS

Figure 1A:
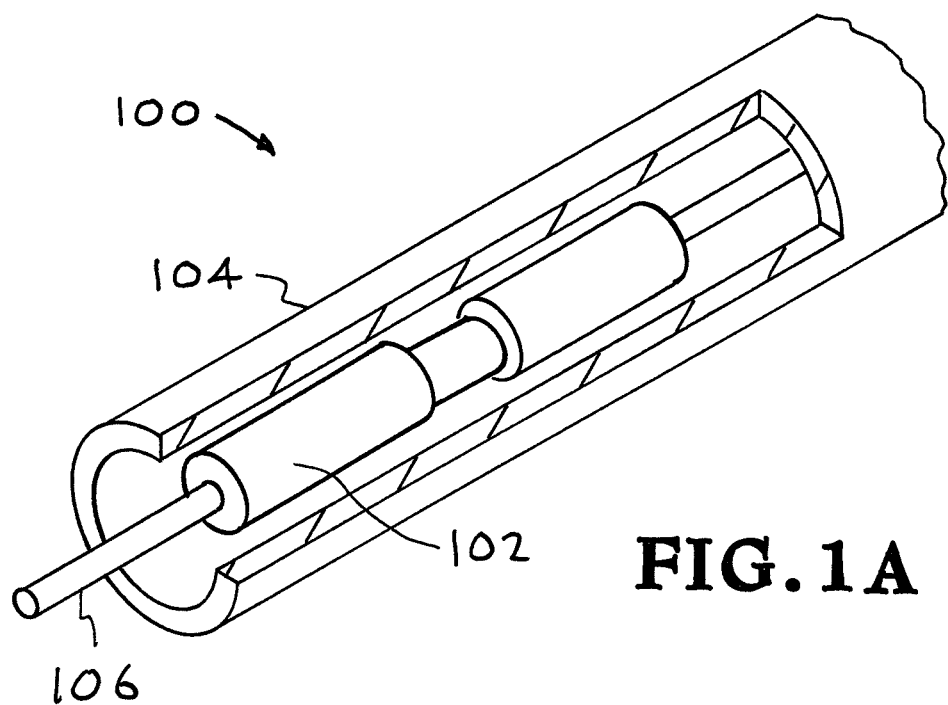
FIGS. 1A and 1B are illustrations of a perspective view (FIG. 1A) and an end view (FIG. 1B) of a device of the invention deployed in a catheter.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

In broad aspect one embodiment of the invention is device for treatment of vascular and septal openings comprising a structure made from biocompatible components, wherein the combined components comprise a structure having two opposing stops or wings, a distal wing and a proximal wing, connected by an axis that is covered by a shape memory polymer foam, wherein the wings when expanded are planar with the surface in which the opening is to be disposed, the wings being larger in surface area than the diameter of the opening and which can be collapsed into a secondary shape that together with the other components of the device may be disposed inside a vascular catheter.

Addressing the clear need of improvement in present devices, the device (of one aspect of this invention) uses a combination of solid components (including neat polymer components) and foam components to achieve a complete seal starting immediately after deployment of the device. Briefly, the device is deployed as a thin cylindrical tube (axis) covered in shape memory foam and having stops or wings on either end across a septal or vascular opening. On actuation or expansion, the wings will open (expand to a desired shape) on either end of the axis to come in close apposition with the septum or vascular wall, positioning itself snugly in the gap. Oversized low-modulus SMP foam (soft, low force), on the middle portion of the axis cylinder, will then expand and optionally axially contract to substantially seal the gap. The device axis foam will either contract due to foam axial contraction while radially expanding and/or the end wings may expand inwardly somewhat to put a small gripping force on the vascular wall surrounding the vascular opening. The wings can be self-expanding or they may be of an SMP requiring actuation so that they expand upon activation. The self-expanding device is generally preferred as the SMP remains in an elastomeric state after deployment, and it is mechanically more compatible with the vascular wall, with less chance of trauma. The wings may also be made of an SMP which has a moisture dependent Tg so it may require actuation via heat or exposure to blood. It will then be elastomeric throughout its deployed life.

As endothelialization of the device occurs in following months, it will optionally and preferably slowly degrade giving way to normal tissue growth and full recovery, if made of biodegradable polymer.

Since this device is designed to be in direct contact with blood throughout its deployed life, it is necessary to consider surface properties of the device for biocompatibility. A non-biocompatible surface, which allows protein adsorption and subsequent formation of platelet plug and blood clot, may eventually dislodge particulates potentially causing fatal emboli downstream. For this purpose two primary parts of the device are considered, a) the foam over the central axis, and b) the wings/stops on either end of the axis, separately.

Modification of the foam surface on the axis may not be as critical as that of the wings for two reasons, a) it is partially removed from direct contact with blood flow in the deployed state of the device, and b) the design of the wings/stops can, optionally, be adequately modified to a mesh-like form to keep any particulates from the foam surface from entering the blood flow. Further the higher surface hydrophilicity due to surface modification, may lead to rapid plasticization and premature actuation of the foam during the delivery of the device. Modification of the surface comprising the wings/stops, on the other hand, is necessary because it is in direct contact with the blood stream in the deployed state. Modification of the wings will not significantly hinder the delivery of the device, since the rate of plasticization of the neat polymer, if used, is expected to be much slower relative to the time scale of the device deployment. Further, it is noteworthy, that any surface modification is not expected to affect the bulk mechanical properties of the material.

Several surface modification means including synthetic hydrophilic surfaces via Poly (ethylene glycol) (PEG) polymers and surfactants, neutral polymers (e.g. Poly(2-hydroxyethyl methacrylate), Polyacrylamide, Poly (n-vinyl-2-pyrrolidone), anionic polymers (Phosphoryl choline polymers), gas discharge deposited coatings specially from PEG like monomers, self assembled n-alkyl molecules with oligo PEG or other polar head groups, have been shown to be non-biofouling with enhanced biocompatibility. In addition, surface modification with natural hydrophilic molecules, including passivating proteins (e.g. albumin, casein), Polysaccharides (e.g. hyaluronic acid), Liposaccharides, Phospholipid bilayers or Glycoproteins (e.g. mucin) is also possible.

Besides preventing any clots from sloughing off the device surface, it is also important to promote endothelialization of the device surface. Otherwise, the long term degradation of the device may release material fragments into the blood stream. This could again lead to potentially fatal downstream emboli. It is envisaged that the endothelialization of the wings/stops will encapsulate the device in the vascular wall from either side of the treated opening. Thereafter, degradation of the material will lead to its gradual bioabsorption into the vascular tissue. Some of the surface modifications which may assist in endothelialization include plasma treatment in argon, oxygen or ammonia environments, conjugation of fibronectin and/or Vascular Endothelial Growth Factor (VEGF) to the material surface, immobilization of natural biomolecules such as gelatin, chitosan, collagen or heparin, or even surface morphology modification to enhance endothelial cell attachment and growth.

Multiple techniques (means) may be used to achieve both, no clot formation, and eventually complete endothelialization of the surface. One method could be to use a passivating layer (e.g. PEG) to limit clot formation, coated on a micropattered surface that may enhance cell attachment and proliferation. Another method may be to use a layer-by-layer method. Here an outer dissolvable coating of a passivating layer (e.g. dip coated polysaccharide or liposaccharide layer) which limits clot formation may be deposited on the device surface, with an underlying layer (e.g. conjugated fibronectin and VEGF) to promote endothelialization. As the passivating layer slowly dissolves, patches of endothelialization promoting surface would be exposed. This would lead to initially sporadic, but eventually complete endothelialization of the device surface as the attached cells integrate with each other.

Example of the Device

Figure 1B:
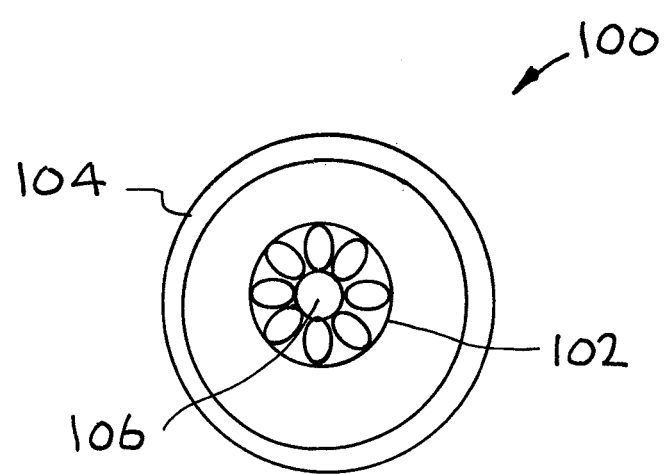
Figure 2A:
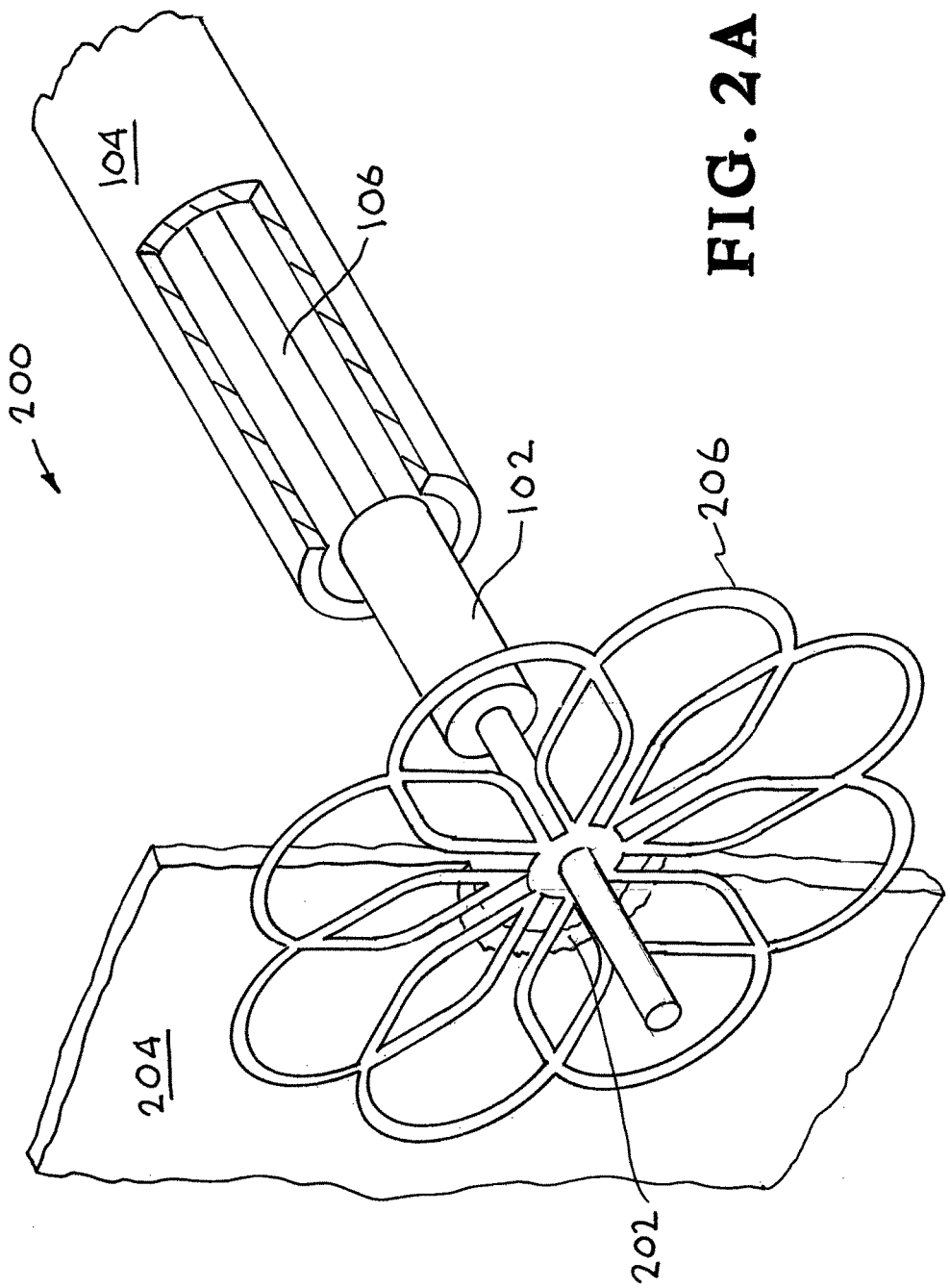
FIGS. 2A and 2B are illustrations of a device of an embodiment of the invention being deployed into the septal opening of a PFO.
Figure 2B:
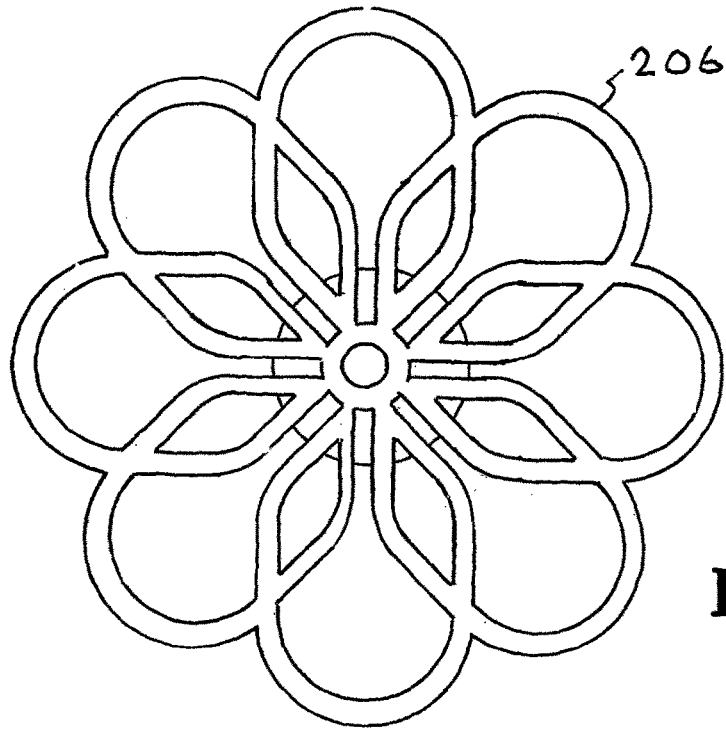

FIGS. 1A and 1B show an artistic depiction of an embodiment of the SMP device design and deployment in treating septal defects. The embodiment is designated generally by the reference numeral 100. The key design features include 1) Self-deploying distal and proximal wings (self expanding or actively actuated SMP) that stabilize the device in the septum; 2) The SMP rubbery modulus (modulus as deployed) can be tailored to 1-100 kPa, which is in the range of the modulus of the myocardium; 3) The deploying wings will preferably match the contour of the septal/myocardial wall; 4) Monolithic device construction of a neat SMP backbone (axis) that includes the two wings and their joining tube; 5) Optional shape recovery in the axial direction that holds the wings tight to both sides of the septal wall with minimal intrusion into the ventricles; 6) SMP foam on the outer surface of the joining axis; 7) SMP open celled foams that act as 100-500 μm (cell size) scaffolds for initial clotting post deployment.

The device 102 of FIGS. 1A and 1B, in one embodiment, is delivered through a 4-5 Fr catheter 104 over a guide wire 106. The design includes a pusher that moves the SMP device over the wire (not shown). The catheter 104 is moved proximally while the device 102 and guide wire 106 are held in place—the distal wing of the SMP deploys (in seconds). If alternative positioning is required, the catheter can be used to re-collapse the distal wing. The catheter 104 and guide wire 106 are retracted together, which deploys the proximal wing and SMP foam scaffolding. The devices 206 and 306 are show in FIGS. 2A, 2B, 3A and 3B in connection with a Patent Foramen Ovale 202 and 302 and an atrial septum 204 and 304.

Figure 3B:
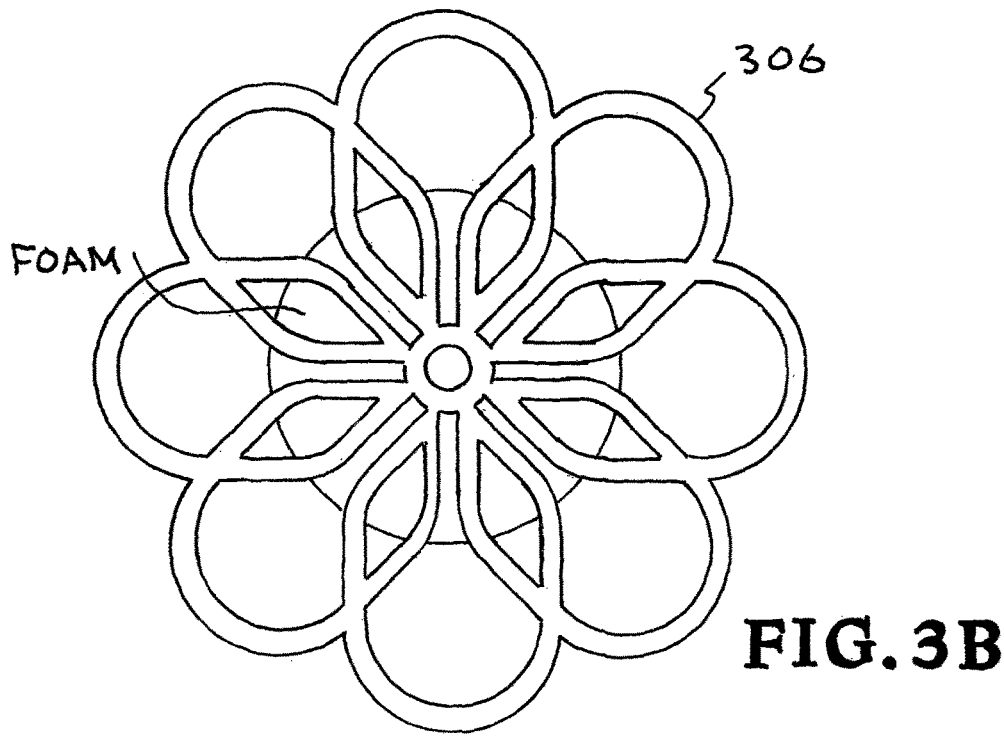
FIGS. 3A and 3B are illustrations of a device of an embodiment of the invention deployed into the septal opening of a PFO.
Figure 3A:
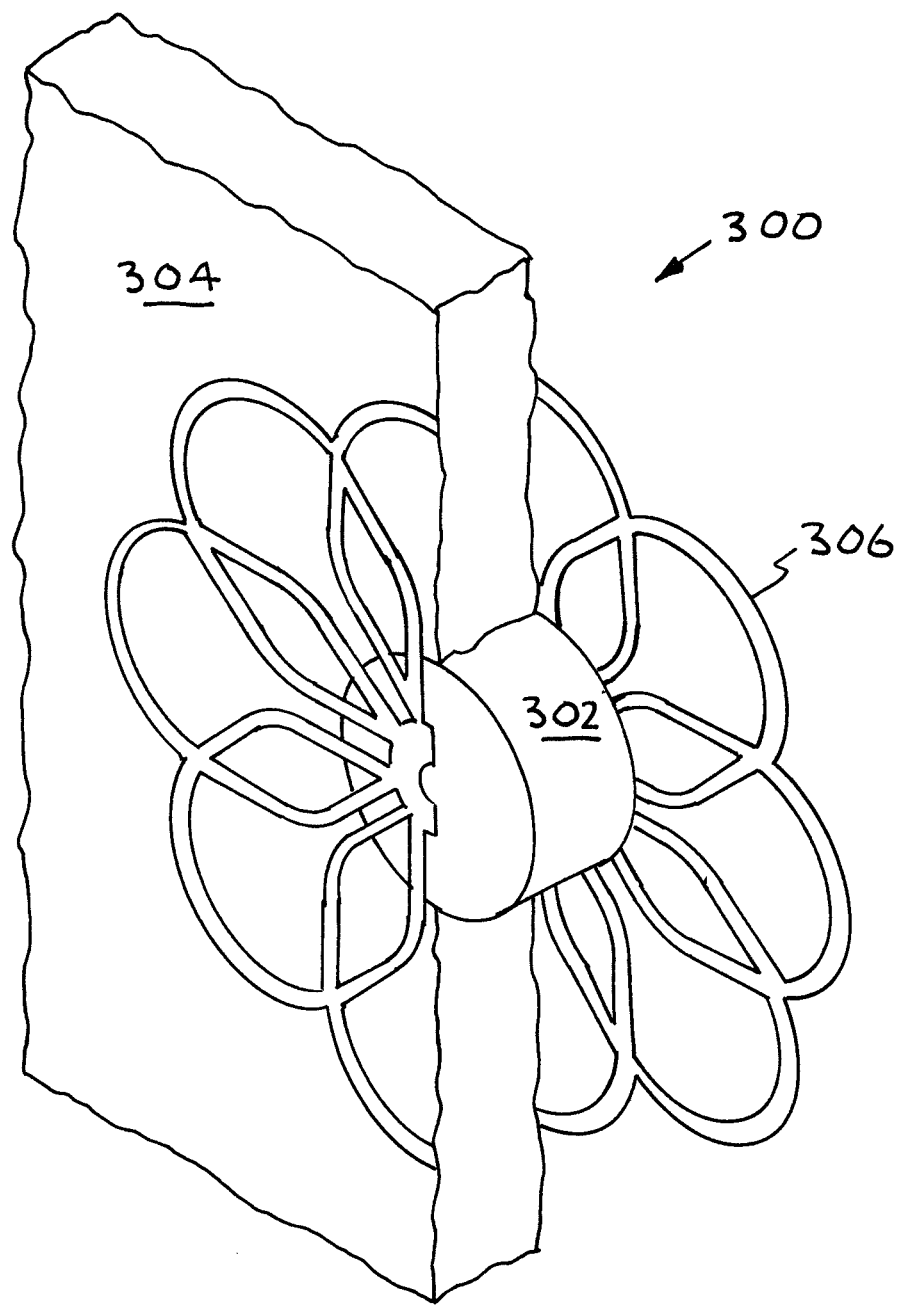

Independent components of the proposed device were manufactured and tested and are illustrated in FIGS. 2A, 2B, 3A and 3B. A possible prototype of the wings was fabricated by micro-injection molding. The design 200 illustrated in FIGS. 2A and 2B collapses into a catheter and then expands (naturally or upon activation of shape memory components at body temperature or other activation) to the design shown. The wing struts are 200 μm wide and the widest diameter is 6 mm. A combination of injection molding and excimer laser machining to produce this design on both ends of a monolithic piece can be used for production of the device. The design 300 is illustrated in FIG. 3A.

The foam will be compressed and bonded to both the inner and outer surfaces of the axis through-tube. SMP foam in its expanded and collapsed forms around a 380 μm guide wire (FIGS. 2A, 2B, 3A, and 3B). The device will use foam on the outer of the central axis. The compressed foam in a 5 Fr catheter is delivered into a defect (ellipse with 6 mm and 4 mm axes). Upon heating to body temperature (or absorption of moisture from blood and heating) the foam expands to fill the eccentric defect opening and optionally to axially contract to pull the wings of the device tight against the defect surface.

FIGS. 2A, 2B, 3A and 3B show components of the proposed device and the device's possible deployment. The PFO device is designed to eliminate long-term shunting and to minimize the protrusion of the device in the heart chamber. This design utilizing a degradable polymer will also result in superior healing response.

The following describes in some more detail the fabrication of an embodiment(s) of the invention.

Fabrication of a PFO Device

Important design parameters include:

1. Ability for delivery through a 5 Fr catheter/sheath (ID 1.4 mm, OD 1.7 mm);
2. Ability to treat a 6-8 mm PFO;
3. Max wing diameter (see FIG. C.1) of 10 mm with strut width of 0.2 mm (FIG. 2); a solid (neat) polymer axis (core) with 0.6 mm diameter and length, between wings, of 4 mm;
4. Actuation of the central core that results in the foam annulus expanding from 1.2 mm outer diameter to 8 mm diameter and the central axis length contracting from 4 mm to 2 mm;
5. Release between the pusher (stiff guide wire, ~0.3 mm diameter) and device (see below).

The PFO device may be fabricated using the following protocol. An aluminum three-part mold machined (Roland 350X CNC) so that the SMP thermoset may be cast in the PFO device (two wings with solid axis). This blank can be machined to reduce the axis diameter. Alternatively, the SMP can be cast in a cylinder and then machined into the device blank. The wings of the blank will then be laser machined into the pattern shown in FIG. 2B. The wings of the machined system will then be collapsed by heating above Tg and drawing through a series of conical tubes (same technique used to make device 306 in FIGS. 3A and 3B). A compressed annulus of foam (same chemistry as neat SMP) will be attached to the axis using a thin coat of the SMP thermoset as an adhesive (neat, foam, and adhesive are all the same material). The device will then be extended with an Instron load frame (in oven above Tg, with extensometer) to lengthen the axis. The wings will be sheathed during the drawing process to keep them collapsed. Finally, the pusher will be attached to the central axis for catheter delivery (See Maitland, D. J., A. Lee, D. Schumann, and L. B. Da Silva, U.S. Pat. No. 6,102,917 Shape Memory Polymer (SMP) Gripper with a Release Sensing System and Maitland, D. J., M. F. Metzger, D. Schumann, A. Lee, and T. S. Wilson, *Photothermal properties of shape memory polymer microactuators for treating stroke.* Lasers In Surgery And Medicine, 2002. 30 (1): p. 1-11 the relevant disclosures of which are incorporated herein by reference).

The preferred device has the Tg of the neat polymer, which includes the wings, to be below body temperature. Thus, the wings will actuate quickly at body temperature. In order to slow the foam deployment for re-sheathing, the foam Tg will be selected to be 45±2° C. Relative to body temperature, this Tg will still be within the breadth of actuation range. The foam will actuate on the order over tens of minutes. Finally, in order to complete the device deployment in a timely fashion, the pusher will be constructed to have a central core that is an optical fiber that delivers optical energy through the solid axis to the foam. The mating joint between the neat polymer axis and the pusher will be designed in one embodiment to detach when the optical energy is used to speed up the foam deployment, which will deploy without the optical energy at a slower rate.

It is desirable that there be good fluoroscopy contrast of the SMP devices. In one embodiment we use platinum (Pt) bands as markers on the PFO device. The Pt markers are placed at the ends of the axis and at 3-4 locations at the outer radius of the wings. However, it is clinically ideal if the SMP can be directly visualized. By doping the SMP with tungsten and/or barium sulfate it is possible to achieve x-ray contrast without negatively affecting the SMP thermo-mechanical properties or photo-thermal properties.

Shape Memory Polymers for Device

The preferred SMP for the device of the invention is a specially tailored, novel, biodegradable SMP. The device is constructed from a combination of shape memory polymer (SMP) components—neat polymer and polymer foams. Polyurethane polymers that will be both biodegradable and bioresorbable will be made of one or more of the base polyols (e.g. TEA, HPED, etc) that have been reacted with other compounds to incorporate into each arm one or more monomers, those monomers incorporating at least one ester linkage into the arm. This ester linkage represents a site for hydrolysis (scission), which is the mechanism for biodegradability/bioresorbability. A preferred SMP is based on hexamethylene diisocyanate (HDI), tetrakis (2-hydroxypropyl)ethylene diamine (HPED), and triethanolamine (TEA). It has the advantages of high recovery stresses, very high shape recovery, sharp actuating transitions, optical clarity, and biocompatibility, but with the addition of controlled biodegradability and benign end products. These advantages are achieved by the incorporation of an ester linkage via the modification of the polyol component (TEA and HPED) with a hydroxyalkanoate group. The most promising hydroxyalkanoate for this purpose is 3-hydroxybutyrate, a molecule that has widely been applied to biodegradable polymer constructs. When used by itself or in combination with other hydroxyalkanoates both the actuation temperature and biodegradation rate may be controlled and tailored. A device constructed from this polymer set is more effective acutely and chronically: acutely due to intrinsic self-deployment during minimally invasive surgery and complete seal via foam, and chronically due to good initial biocompatibility with biocompatible degradation products.

Hexamethylene diisocyanate (HDI) is preferred for the isocyanate group in one embodiment for the polymer of the invention as it is a small aliphatic compound and is known to be adequate for use in biodegradable biomedical applications. Hydroxyalkanoate (e.g. 3-hydroxybutyrate) modified TEA and HPED are preferred as the branched polyols with tri- and tetra functional molecules because they give the dual benefit of high functionality with biocompatible end products. Actuation transition, biodegradation rate, and hydrophilicity of the SMP may be tuned by selection of the hydroxyalkanoate type and number of groups per polyol arm. Some formulations will utilize 3-hydroxybutyrate (HB) in molar ratios of HB to hydroxyl (from TEA or HPED) groups from 2:3 to 9:1 HB to polyol OH groups. Since HB can also self condense, for TEA this means having from 2/3 to 9 hydrolyzable ester linkages per arm on an average. Additional control over biodegradation rate, transition temperature, and hydrophilicity may be obtained through the use of HB combined with other hydroxyalkanoates. Additional hydroxyalkanoate options, include ε-caprolactone, lactic acid, and glycolic acid. Further transition temperature modulation of these new formulations, can be achieved through addition of trimethylhexamethylenediisocyanate (TMHDI) with HDI, as in the methodology previously established in our laboratory.

Example of Synthesis and Characterization

A preferred SMP polymer is polyurethane with soft segment core of trifunctional TEA. In one embodiment the hydroxyl containing arms of TEA are capped with a single hydroxybutyrate molecule (on average) via ester bond formation. Crosslinked SMP is then generated by combining the HB modified TEA (tris(3-hydroxyethylbutyrate)amine) with HDI in 1:1 hydroxy group to isocyanate group stoichiometric ratios. Polymer synthesis is performed via the following steps: i) Endcapping the TEA with 3-hydroxybutyrate; ii) preparing the neat polymer; iii) preparing the foam.

(i) Encapping of TEA with HB—TEA is endcapped with HB using a protocol adapted from West et al. (West, J. L. and J. A. Hubbell, *Polymeric biomaterials with degradation sites for proteases involved in cell migration*. Macromolecules, 1999. 32 (1): p. 241-244.) Briefly, dicyclohexylcarbodiimide (DCC) is used to activate the carboxyl group of the HB for subsequent reaction with TEA. Anhydrous pyridine is then used to initiate the formation of an ester link between the hydroxyl endgroups of TEA and the activated carboxyl group of the HB, FIG. 4. The precipitated dicyclohexylurea is removed with vacuum filtration and the polymer solution is washed with distilled water.

Figure 4:
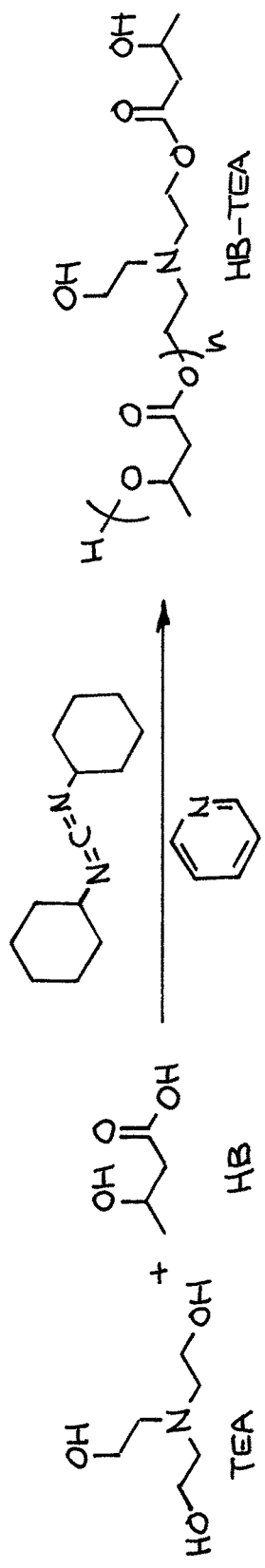
FIG. 4 is a schematic of the synthesis of HB-TEA.

In FIG. 4 note variability in number of HB groups per arm, which depend on TEA:HB ratio and reaction statistics. This provides one factor for control of biodegradation rate. Following solvent removal by rotary evaporation, the polymer is dried in vacuo. The addition of HB will be confirmed with infrared spectroscopy (C=O, ester at 1730 cm−1) and quantified using NMR spectroscopy.

Figure 5:
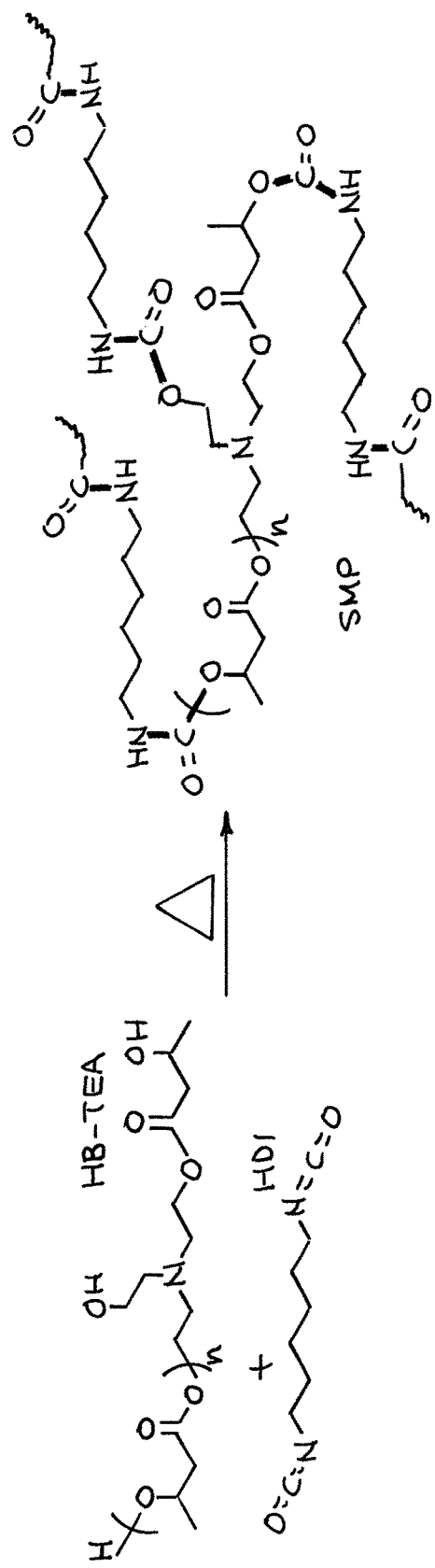
FIG. 5 is a schematic of the polymer network showing the structure of a network formed around a TEA center for HB modified TEA and HDI.

(ii) Preparation of neat SMP—Neat SMPs are synthesized and cast into both test specimens as well as prototype devices from the thermosetting reaction of constituent monomers via liquid casting. The HB modified TEA monomer (liquid) and HDI (diisocyanate) are weighed in a glove box using a stoichiometric (1:1) ratio of hydroxyl to isocyanate groups. The mixture is then sonicated to remove bubbles, vacuum degassed to remove residual dissolved gas, and liquid injection molded into test samples and prototype devices from syringe. The cast parts are cured using a temperature profile of 60 minutes at room temperature, followed by a ramp to 130° C. at 30° C./hour, followed by 1 hour at 130° C. all under a nitrogen atmosphere. Parts are allowed to cool slowly under nitrogen, removed from the molds, and stored in glass bottles or polybags under dessication prior to testing. FIG. 5 shows a schematic of the polymer network showing the structure of a network formed around a TEA center for HB modified TEA and HDI. Medium time hydrolyzable bonds are e —O—C(=O)— (ester linkages), and long term degradable bonds are —(H) N—C(=O)—O— (urethane linkages).

(iii) Preparation of SMP Foam—SMPs foams can be fabricated according to procedures previously reported by (Wilson, T. S, and J. P. Bearinger, New Shape Memory Polymers; US Application 2006/0036045, Feb. 16, 2006) Briefly, a prepolymer will be made by mixing HDI and the HB-TEA polyol at ratios in the range of 1:0.30-0.40 of isocyanate to hydroxyl groups, with the final ratio determined by prepolymer viscosity (target 50 Pa's). The prepolymer reaction is allowed to proceed for 2 hours at 25° C. followed by 24 hours at 50° C. Foams are then made by mixing in order 32 grams prepolymer with 1.5 grams Dabco DC-5169 (Air Products), 1.5 grams DC-4000 (Air Products), 6 grams HB-TEA, 1.1 grams water, 270 ul of a mixture of Dabco BL-22 and T-131 catalysts (in 2.5:1 ratio), and 3 ml of Enovate 3000 (Honeywell) blowing agent. All components except catalyst and Enovate are mixed vigorously for 2 minutes.

The catalyst and Enovate are next added, mixed vigorously for 15 seconds, and placed in an oven at 90 C for 20 minutes. The foams are allowed to room temperature cure for 24 hours and are then subjected to simultaneous dilute acid etching and sonication to open the remaining closed cells. Foams are dried under vacuum and packaged for storage prior to testing.

Control of the Material Properties

Control of the existing neat SMPs is accomplished through variation in monomer composition. This can be done with either the diisocyanate blend (using combinations of HDI and TMHDI) or in the composition of the polyol blend. In a preferred polymer of this invention, variation of polyol composition will be achieved through both the use of 3-hydroxybutyrate and 6-hydroxyhexanoate monomers. Since simultaneous control of biodegradation rate is needed, both isocyanate and polyol variation will be employed as previously discussed. Also, additional control over biodegradation rate can be achieved by control of arm length, which defines the number of ester links per branch and therefore the availability of cleavage sites. The use of hydroxyalkanoates, which can self-condense, facilitates this.

Changing Shape Fixity, Expansion Ratio, and Recovery Stress

An 8 mm sample of foam is cut out using a biopsy punch for measuring the fixity and expansion ratio. This sample is crimped using the SC150-42 Stent Crimper (Machine Solutions) set at temperature above the Tg of the material. The crimped sample is then allowed to cool to below its Tg; its dimensions measured immediately and at 24, 48, and 120 hours to determine fixity. Thereafter recovery is measured by heating the foam back to above its Tg. Results are analyzed by means of±standard deviation (n=3). Recovery stresses are measured on foam samples using either ARES LS-2 rheometer or an Instron equipped with a thermal oven.

Cubic foam samples are pre-compressed 30° C. above their Tgs, and cooled under compression. After storage at room temperature at times above, they are placed in compression fixtures at the point of contact and reheated to 30° C. above Tg. After thermal equilibration (5 minutes), the compressive strain are ramped to zero while expansion forces exerted by the foams are simultaneously measured. This provides a direct measure of recovery forces expected to act on the periphery of the PFO.

System of the Invention

In one aspect the invention is a system that utilizes the above described device(s) in the closure and treatment of vascular and septal openings The system will include a device as described above; a catheter to carry the device when it is in its secondary shape to the location of deployment; optionally, a carrier wire on which the device is carried inside the catheter in its secondary shape; a pusher to move the device through the catheter into the desired location; and a releasable connector that connects the device to the pusher. The components of an embodiment of this system are illustrated in FIGS. 1-3. The system may include a tube or sub-catheter that fits inside the delivery catheter into which the device is disposed. This allows the device in its secondary shape (collapsed to fit inside a catheter) to be preassembled for use in a conventional delivery catheter.

Method of the Invention

In another aspect the invention is a method of treating or closing vascular or septal openings such as PFO. Exemplary of a method of the invention (referring to FIGS. 1A, 1B, 2A, and 2B); a device as described above is delivered to the opening to be treated through a catheter (for example a 4-5 Fr catheter) over a guide wire. The system includes a pusher that moves the device over the wire. The catheter is moved proximally while the device and guide wire are held in place—the distal wing of the SMP deploys (in seconds). If alternative positioning is required, the catheter can be used to re-collapse the distal wing. The catheter and guide wire are retracted together, which deploys the proximal wing and SMP foam scaffolding.

A primary design consideration is the clinician's (who will use the system of the invention) desire to expand, collapse, re-expand, re-collapse (repeat) the device while visualizing its placement relative to septal defect. The system of this invention permits the distal wing to be deployed and collapsed, via re-sheathing, as many times as the clinician desires. That is, until the central foam is deployed. The re-sheathing of foam can be accomplished as long as 1. The proximal end of the foam does not exit the sheath and 2. Significant clotting has not occurred. Given that clotting that may prevent re-collapse of foam can occur in minutes, it is possible to prevent the foam from expanding too quickly by using a slightly foam Tg that is ~10° C. above body temperature (the activating mechanism of a preferred embodiment).

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A device, to treat at least one of a vascular and septal opening, comprising biocompatible components, wherein:

the components comprise a structure having two opposing wings, a distal wing and a proximal wing, coupled to each other by an axis that is covered by a covering comprising a shape memory polymer foam, the wings, when expanded, are configured to be: generally planar with a surface in which the opening is to be disposed, and larger in surface area than a diameter of the opening, and the distal wing, when expanded, is configured to be collapsible into a secondary shape that together with the other components of the device may be disposed inside a vascular catheter, the wings comprise neat, unfoamed, shape memory polymer, the device is configured to be secured in the opening by longitudinal shrinkage, along a long axis of the axis, of an additional shape memory polymer included in the axis, the additional shape memory polymer is different from, but coupled to, the covering that comprises the shape memory polymer foam, and the shape memory polymer foam is located on the additional shape memory polymer.

2. The device of claim 1 wherein the shape memory polymer foam is biodegradable.

3. The device of claim 1 wherein the shape memory polymer is polyurethane.

4. The device of claim 1 wherein the entire device is constructed of biodegradable, bioresorble shape memory polymers.

5. The device of claim 1 wherein the surface of at least one of the components is configured to limit foreign body reaction and prevent dislodging of particulates into the blood flow.

6. The device of claim 5 wherein the surface of the at least one of the components is also configured to promote endothelialization of the device and its bioresorption into the vascular tissue.

7. The device of claim 1 wherein the surface of at least one of the components is configured to promote endothelialization of the device and its bioresorption into the vascular tissue.

8. A system comprising:
the device of claim 1;
a catheter to carry the device when it is in its secondary shape to the location of deployment;
a carrier wire on which the device, when it is in its secondary shape, is carried inside the catheter;
a pusher to move the device into the desired location;
a releasable connector that connects the device to the pusher;
wherein the device is disposed inside a cylindrical sheath that is disposed inside the catheter.

9. The device of claim 1, wherein the neat, unfoamed, shape memory polymer of at least one of the distal and proximal wings has a first glass transition temperature (Tg) and the shape memory polymer foam has a second Tg that is unequal to the first Tg.

10. The device of claim 9, wherein the first Tg is lower than the second Tg.

11. The device of claim 10, wherein the first Tg is no greater than 37 degrees C. and the second Tg is greater than 37 degrees C.

12. The device of claim 11, wherein the wings are configured to actuate more quickly at the first Tg than the shape memory polymer foam is configured to actuate at the second Tg.

13. The device of claim 11, wherein the shape memory polymer foam is configured to take more than 10 minutes to actuate once the second Tg is reached.

14. The device of claim 10 including an optical fiber coupled to the axis to communicate optical energy to the axis.

15. The device of claim 14 comprising a pusher rod and a releasable connector that couples the pusher rod device to the axis, wherein the pusher rod includes the optical fiber.

16. The device of claim 15, wherein the axis is solid and configured to communicate optical energy.

17. The device of claim 9, wherein the shape memory polymer foam includes hydroxybutyrate (HB) modified triethanolamine (TEA).

18. The device of claim 9, wherein the shape memory polymer foam: (a) is a thermally actuated shape memory polymer, which (a)(i) transforms from a stable secondary shape to a predetermined primary shape, and (a)(ii) has a shape-fixing matrix phase and a shape memorizing dispersed phase; and (b) the secondary shape is determined when the shape memory polymer foam is above the second Tg.

19. The device of claim 9, wherein the additional shape memory polymer is monolithic with the wings that are made of neat, unfoamed, shape memory polymer.

20. The device of claim 1, wherein (a) an outermost surface of the neat, unfoamed, shape memory polymer of the wings is treated with an endothelialization agent, (b) the endothelialization agent is covered with a dissolvable coating of a passivation layer, and (c) the endothelialization agent is based on at least one of argon, oxygen, ammonia, fibronectin, Vascular Endothelial Growth Factor (VEGF), gelatin, chitosan, collagen, and heparin.

21. A device, to treat at least one of a vascular and septal opening, comprising biocompatible components wherein:
the components comprise a structure having distal and proximal wings coupled to each other by an axis that is covered by a covering comprising a shape memory polymer foam,
one or more portions of the wings, when expanded, are collectively configured to be: (a)(i) generally planar and generally parallel with another plane that defines at least a portion of a surface that includes the opening, and (a)(ii) larger in surface area than a diameter of the opening, and
the distal wing, when expanded, is configured to be: (b)(i) collapsible into a secondary shape, and (b)(ii) disposed inside a vascular catheter when in the secondary shape,
the wings comprise a shape memory material,
the device is configured to be secured in the opening by longitudinal shrinkage, along a long axis of the axis, of an additional shape memory polymer included in the axis,
the additional shape memory polymer is different from, but coupled to, the covering that comprises the shape memory polymer foam, and
the shape memory polymer foam is located on the additional shape memory polymer.

22. The device of claim 21 wherein:
the shape memory polymer foam: (a) is a thermally actuated shape memory polymer, which (a)(i) transforms from a stable secondary shape to a predetermined primary shape, and (a)(ii) has a shape-fixing matrix phase and a shape memorizing dispersed phase, and (b) includes triethanolamine (TEA); and
the secondary shape of the shape memory polymer foam is determined when the shape memory polymer foam is above a glass transition temperature (Tg).

* * * * *